United States Patent [19]

Stephen

[11] 3,941,746

[45] Mar. 2, 1976

[54] CONTAINING HINDERED PHENOLIC NORBORNANE-2,3-DICARBOXIMIDES STABILIZED COMPOSITIONS

[75] Inventor: John F. Stephen, New City, N.Y.

[73] Assignee: Ciba-Geigy Corporation, Ardsley, N.Y.

[22] Filed: May 30, 1975

[21] Appl. No.: 582,564

Related U.S. Application Data

[62] Division of Ser. No. 429,235, Dec. 28, 1973.

[52] U.S. Cl. .................... 260/45.8 N; 260/45.8 A
[51] Int. Cl.² ........................................... C08J 3/20
[58] Field of Search ................. 260/45.8 N, 45.8 A

[56] References Cited
UNITED STATES PATENTS

| | | | |
|---|---|---|---|
| 2,489,000 | 11/1949 | Valentino | 260/45.8 N |
| 3,340,225 | 9/1967 | Dressler et al. | 260/45.8 N |
| 3,734,926 | 5/1973 | Dexter | 260/45.8 N |
| 3,746,721 | 7/1973 | Stephen | 260/45.8 N |
| 3,790,597 | 2/1974 | Dexter et al. | 260/45.8 N |

Primary Examiner—V. P. Hoke
Attorney, Agent, or Firm—Nestor W. Shust

[57] ABSTRACT

Compounds having the formula

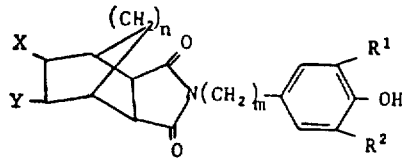

wherein $R^1$ and $R^2$ are lower alkyl, X and Y are hydrogen or, when taken together, they form a bond or an ether linkage, $m$ is 0 to 3, and $n$ is 0 to 2, are good ultraviolet light stabilizers for synthetic polymers.

4 Claims, No Drawings

CONTAINING HINDERED PHENOLIC NORBORNANE-2,3-DICARBOXIMIDES STABILIZED COMPOSITIONS

This is a division of application Ser. No. 429,235 filed on Dec. 28, 1973.

DETAILED DISCLOSURE

This invention relates to hindered phenolic norbornane-2,3-dicarboximides and organic compositions stabilized therewith. More specifically, these compounds are useful as stabilizers of organic materials which are subject to ultraviolet light degradation. The compounds of this invention can be represented by the formula

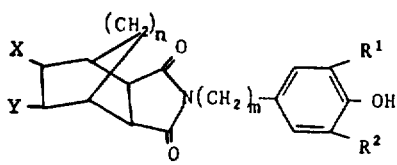

wherein
  $R^1$ and $R^2$ are the same or different (lower) alkyl groups of 1 to 4 carbon atoms,
  X and Y are hydrogen or, when taken together, they form a bond or an ether linkage,
  $m$ has a value of 0 to 3, and
  $n$ has a value of 0 to 2.

The $R^1$ and $R^2$ groups can be any straight or branched chain alkyl having 1 to 4 carbon atoms, such as methyl, ethyl, isopropyl, n-butyl and tert-butyl. Preferably these groups are methyl, isopropyl and tert-butyl groups. Most preferably both groups are tert-butyl.

The X and Y groups can be hydrogen or, when taken together, they may form a bond or an ether linkage. In other words, when they form a bond there will be a double bond between positions 5 and 6. When they form an ether linkage, an epoxy group would result.

Imides of the formula I wherein $m$ is 0, 2, 3 and X and Y are hydrogen, and X and Y taken together form a bond can be prepared by reacting the appropriate anhydride with an appropriate amine of the formula

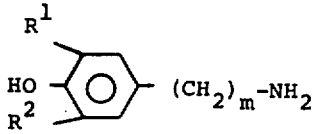

wherein $R^1$ and $R^2$ are as defined previously.

The 3,5-dialkyl-4-hydroxyphenyl substituted amines wherein $m$ is 0 can be prepared as described in U.S. Pat. No. 3,198,797. The amine wherein $m$ is 2 can be prepared, for example, through chloromethylation of a dialkylphenol as described in U.S. Pat. No. 2,838,571, followed by treatment of the resulting chloromethyl derivative with sodium or potassium cyanide, and reduction of the resultant dialkylhydroxyphenylacetonitrile to the amine. The amine when $m$ is 3 can be prepared by reducing the appropriate 3-(3,5-dialkyl-4-hydroxyphenyl)propionitrile with lithium aluminim hydride to yield the corresponding amine. The nitrile can be prepared according to the method described in U.S. Pat. No. 3,121,732 wherein the appropriate dialkylphenol is reacted with acrylonitrile.

Compounds of formula I wherein $m$ is 1 and X and Y are hydrogen, X and Y taken ogether form a bond and X and Y taken together form an ether linkage can be prepared by reacting the appropriate imide with the appropriate 3,5-dialkyl-4-hydroxybenzyldialkylamine of the formula

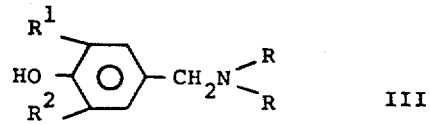

wherein $R^1$ and $R^2$ are as defined previously and R is an alkyl group such as methyl or ethyl in a suitable solvent such as N,N-dimethylformamide. The 3,5-dialkyl-4-hydroxybenzyldialkyl amines can be prepared as described by E. P. Previc et al., Industrial and Engineering Chemistry, 53, 469 (1961).

The compounds of formula I wherein $m$ is 0, 1, 2 and 3 and X and Y are both hydrogen can also be prepared by catalytic hydrogenation of the corresponding compounds of formula I wherein X and Y taken together form a bond in the presence of a suitable catalyst such as palladium on charcoal.

The compounds of formula I wherein $m$ is 0, 2 and 3 and X and Y taken together form an ether linkage can be prepared by oxidizing the corresponding compounds of formula I wherein X and Y taken together form a bond with a suitable oxidant, such as hydrogen peroxide and various peracids such as peracetic and m-chloroperbenzoic acids.

5-Norbornene-endo-2,3-dicarboxylic anhydride, cis-$\Delta^4$-tetrahydrophthalic anhydride, bicyclo[2.2.2]oct-5-eneendo-2,3-dicarboxylic anhydride are commercially available.

cis-Hexahydrophthalic anhydride is commercially available. Norbornane-endo-2,3-dicarboxylic anhydride can be prepared by catalytic reduction of 5-norbornene-endo-2,3-dicarboxylic anhydride. Bicyclo[2.2.2]oct-5-ane-endo-2,3-dicarboxylic anhydride can be prepared by the procedure outlined in British Patent Number 796,133.

cis-Hexahydrophthalimide is commercially available. Norbornane-endo-2,3-dicarboximide can be prepared by catalytic reduction of 5-norbornene-endo-2,3-dicarboximide using a suitable catalyst such as palladium on charcoal. 5-Norbornene-endo-2,3-dicarboximide can be prepared by the procedure described by W. S. Worrall in J. Amer. Chem. Soc., 82, 5707 (1960). Bicyclo[2.2.2]octane-endo-2,3-dicarboximide and bicyclo[2.2.2]oct-5-ene-2,3-dicarboximide can be prepared as described by F. Manabu and O. Keiko, Chem., Pharma. Bull. (Tokyo) 10, 714 (1962).

cis-$\Delta^4$-tetrahydrophthalimide is commercially available.

Exo-5,6-epoxynorbornane-endo-2,3-dicarboximide can be prepared, for example, by the procedure of W. S. Worrall, J. Amer. Chem. Soc., 82, 5707 (1960). 4,5-Epoxycyclohexane-1,2-dicarboximide can be prepared by the procedure described in U.S. Pat. No. 2,897,208. Exo-5,6-epoxybicyclo[2.2.2]octane-endo-2,3-dicarboximide can be prepared by peracid oxidation of bicyclo[2.2.2]oct-5-ene-endo-2,3-dicarboximide.

The following examples further illustrate the preparation of the compounds without introducing any limitations.

EXAMPLE 1

N-(3,5-di-tert-butyl-4-hydroxyphenyl)-5-norbornene-endo-2,3-dicarboximide

In a nitrogen atmosphere, a stirred solution of 5-norbornene-endo-2,3-dicarboxylic anhydride (12.3 g, 0.075 mole) and 2,6-di-tert-butyl-4-aminophenol (16.7 g, 0.075 mole) in 150 ml of xylene was heated under reflux for 6 hours, water being removed with a Dean-Stark trap. The xylene was evaporated under reduced pressure and the residue was triturated with hexane-benzene mixture. The resulting solid was filtered off and was recrystallized from ethanol to give 12.3 g (45%) of the desired imide, m.p. 200°–202°.

Following the above procedure N-(3,5-dimethyl-4-hydroxyphenyl)-5-norbornene-endo-2,3-dicarboximide is prepared by employing the appropriate starting materials.

EXAMPLE 2

N-(3,5-di-tert-butyl-4-hydroxyphenyl)-norbornane-endo-2,3-dicarboximide

N-(3,5-di-tert-butyl-4-hydroxyphenyl)-5-norbornene-endo-2,3-dicarboximide (5.5 g, 0.015 mole) was dissolved in 200 ml of ethanol and hydrogenated over 100 mg of 10% palladium on charcoal in a Parr apparatus at 50 psi. The catalyst was removed by filtration and the filtrate was evaporated under reduced pressure. Recrystallization of the resulting solid form benzene-heptane gave 4.8 g (88%) of N-(3,5-di-tert-butyl-4-hydroxyphenyl)-norbornane-endo-2,3-dicarboximide, m.p. 184°–186°.

Following the above procedure N-(3-methyl-5-tert-butyl-4-hydroxyphenyl)-norbornane-endo-2,3-dicarboximide is prepared when the appropriate starting materials are used.

EXAMPLE 3

N-(3,5-di-tert-butyl-4-hydroxybenzyl)-norbornane-endo-2,3-dicarboximide

In a nitrogen atmosphere, a stirred solution of norbornane-endo-2,3-dicarboximide (13.0 g, 0.079 mole) and 2,6-di-tert-butyl-4-dimethylaminomethylphenol (21.7 g, 0.083 mole) in 100 ml of N,N-dimethylformamide was heated at 120°–125° for 4 hours. Upon cooling the mixture was poured into water and the precipitated solid was taken up in ether. The ether solution was washed with dilute hydrochloric acid and then water. The dried ($Na_2SO_4$) solution was evaporated under reduced pressure and the solid residue was recrystallized from methanol to give 19.0 g (50%) of the title imide, m.p. 158°–160°.

Following the above procedure (N-(3,5-diisopropyl-4-hydroxybenzyl)-norbornane-endo-2,3-dicarboximide is prepared when the appropriate starting materials are employed.

EXAMPLE 4

N-(3,5-di-tert-butyl-4-hydroxyphenyl)-exo-5,6-epoxy-norbornane-endo-2,3-dicarboximide A stirred mixture of N-(3,5-di-tert-butyl-4-hydroxyphenyl)-5-norbornene-endo-2,3-dicarboximide (5.5 g, 0.015 mole) 25 ml of formic acid and 25 ml of methylene chloride was treated with 31.5% hydrogen peroxide solution (3.4 g, 0.03 mole) and the mixture was heated at 40°–45° for 18 hours. The solvent mixture was stripped off and the residue was dissolved in ether. The ether solution was washed with 10% aqueous sodium bicarbonate solution and then water. The dried solution was evaporated and the residue recrystallized from methanol-water to give 2.5 g (43.5%) of the desired epoxide, m.p. 158°–160°.

Following the above described procedures and employing the above described starting materials, the compounds reported in Table I have been prepared.

TABLE I

| Ex. No. | X,Y | n | m | m.p.°C |
|---|---|---|---|---|
| 5 | $\Delta^{5,6}$ | 1 | 1 | 139–141 |
| 6 | $\Delta^{5,6}$ | 1 | 2 | 221–223 |
| 7 | $\Delta^{5,6}$ | 1 | 3 | 112–114 |
| 8 | $\Delta^{5,6}$ | 0 | 0 | 154–156 |
| 9 | H,H | 2 | 1 | 159–161 |
| 10 | H,H | 0 | 0 | 127–128 |
| 11 | H,H | 0 | 1 | 139–141 |
| 12 | epoxy | 0 | 0 | 159–162 |
| 13 | epoxy | 1 | 1 | 181–183 |

*The designation + in the above formula means tert-butyl group.

The compounds of this invention are stabilizers of organic material normally subject to thermal, oxidative or actinic light deterioration. Materials which are thus stabilized include synthetic organic polymeric substances including homopolymers, copolymers, and mixtures thereof, such as vinyl resins formed from the polymerization of vinyl halides or from the copolymerization of vinyl halides with unsaturated polymerizable compounds, e.g., vinyl esters, $\alpha,\beta$-unsaturated acids, $\alpha,\beta$-unsaturated esters, $\alpha,\beta$-unsaturated ketones, $\alpha,\beta$-unsaturated aldehydes and unsaturated hydrocarbons such as butadienes and styrene; poly-$\alpha$-olefins such as high and low density polyethylene, cross-linked polyethylene, polypropylene, poly(4-methylpentene-1 and the like, including copolymers of $\alpha$-olefins; such as ethylene-propylene copolymers, and the like; dienes such as polybutadiene, polyisoprene, and the like, including copolymers with other monomers; polyurethanes such as are prepared from polyols and organic polyisocyanates, and polyamides such as polyhexamethylene adipamide and polycaprolactam; polyesters such as polyethylene terephthalates; polycarbonates such as those prepared from bisphenol-A and phosgene; polyacetals such as polyethylene terephthalate polyacetal; polystyrene, polyethyleneoxide; polyacrylics such as polyacrylonitrile; polyphenyleneoxides such as those prepared from 2,6-dimethylphenol and the like; and copolymers such as those of polystyrene containing copolymers of butadiene and styrene and those formed by the copolymerization of acrylonitrile, butadiene and/or styrene.

Other materials which can be stabilized by the compounds of the present invention include lubricating oil of the aliphatic ester type, i.e., di(1,2-ethylene)-azelate, pentaerythritol tetracaproate, and the like; animal and vegetable derived oils, e.g., linseed oil, fat, tallow, lard, peanut oil, cod liver oil, castor oil, palm oil, corn oil, cottonseed oil, and the like; hydrocarbon materials such as gasoline, mineral oil, fuel oil, drying oil, cutting fluids, waxes, resins, and the like, salts of fatty acids such as soaps and the like; and alkylene glycols, e.g., β-methoxyethyleneglycol, methoxytriethyleneglycol, triethylene glycol, octaethyleneglycol, dibutyleneglycol, dipropyleneglycol and the like.

The compounds of this invention are particularly useful as UV light stabilizers, especially for the protection of polyolefins, for instance, polyethylene, polypropylene, poly(butene-1), poly(pentene-1), poly(3-methylbutene-1), poly(4-methylpentene-1), various ethylene-propylene copolymers and the like.

In general, the stabilizers of this invention are employed from about 0.01 to about 5% by weight of the stabilized composition, although this will vary with the particular substrate and application. An advantageous range is from about 0.05 to about 2% and especially 0.1 to about 1%.

For addition to polymeric substrates, the stabilizers can be blended before polymerization or after polymerization, during the usual processing operations, for example, by hot-milling, the composition then being extruded, pressed, blow molded or the like into films, fibers, filaments, hollow spheres and the like. The heat stabilizing properties of these compounds may advantageously stabilize the polymer against degradation during such processing at the high temperature generally encountered. The stabilizers can also be dissolved in suitable solvents and sprayed on the surface of films, fabrics, filaments or the like to provide effective stabilization. Where the polymer is prepared from a liquid monomer as in the case of styrene, the stabilizer may be dispersed or dissolved in the monomer prior to polymerization or curing.

These compounds can also be used in combination with other additives such as antioxidants, sulfercontaining esters such as distearyl-β-thiodipropionate (DSTDP), dilauryl-β-thiodipropionate (DLTDP) in an amount of from 0.01 to 2% by weight of the organic material, and the like, pourpoint depressants, corrosion and rust inhibitors, dispersing agents, demulsifiers, antifoaming agents, fillers such as glass or other fibers, carbon black, accelerators and the other chemicals used in rubber compounding, plasticizers, color stabilizers, di- and tri-alkyl- and -alkylphenylphosphites, heat stabilizers, ultraviolet light stabilizers, antiozonants, dyes, pigments, metal chelating agents, dyesites and the like. Often combinations such as these, particularly the sulfur containing esters, the phosphites and/or the ultraviolet light stabilizers will produce superior results in certain applications to those expected by the properties of the individual components.

The following formula represents co-stabilizers which are in certain instances very useful in combination with the stabilizers of this invention:

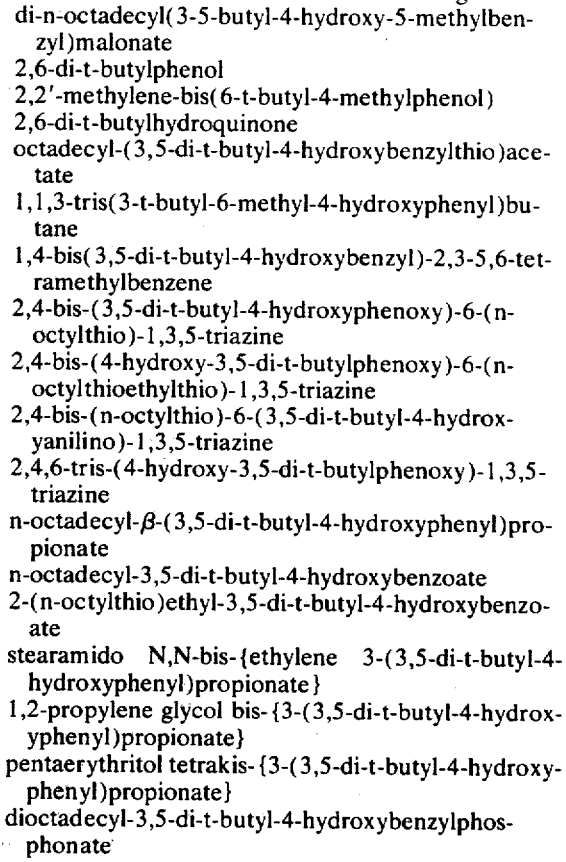

wherein R is an alkyl group having from 6 to 24 carbon atoms; and n is an integer from 1 to 6. Especially useful compounds of this type are dilauryl-β-thiodipropionate and distearyl-β-thiodipropionate. The above co-stabilizers are used in the amount of from 0.01 to 2% by weight of the organic material, and preferably from 0.1 to 1%.

Although the compounds of this invention may to some degree also be effective as thermal stabilizers, if the processing of the polymer is carried out at high temperatures it is advantageous to incorporate additional antioxidants.

In most applications, it is desirable to incorporate into the resin composition, sufficient thermal antioxidants to protect the plastic against thermal and oxidative degradation. The amount of antioxidant required will be comparable to that of the actinic stabilizer. Namely, from about 0.005% to 5% and preferably from 0.01% to 2% by weight Representative of such antioxidants are phosphite esters, such as triphenylphosphite and dibutylphosphite and alkyl arylphosphites such as dibutylphenylphosphite, and the like.

The best results have been obtained with the preferred class of thermal antioxidants, the hindered phenols. These compounds have been found to provide the best thermal stabilization with the least discoloration in the compositions of the invention. Amoung these phenolic antioxidants are included the following:

di-n-octadecyl(3-5-butyl-4-hydroxy-5-methylbenzyl)malonate
2,6-di-t-butylphenol
2,2'-methylene-bis(6-t-butyl-4-methylphenol)
2,6-di-t-butylhydroquinone
octadecyl-(3,5-di-t-butyl-4-hydroxybenzylthio)acetate
1,1,3-tris(3-t-butyl-6-methyl-4-hydroxyphenyl)butane
1,4-bis(3,5-di-t-butyl-4-hydroxybenzyl)-2,3-5,6-tetramethylbenzene
2,4-bis-(3,5-di-t-butyl-4-hydroxyphenoxy)-6-(n-octylthio)-1,3,5-triazine
2,4-bis-(4-hydroxy-3,5-di-t-butylphenoxy)-6-(n-octylthioethylthio)-1,3,5-triazine
2,4-bis-(n-octylthio)-6-(3,5-di-t-butyl-4-hydroxyanilino)-1,3,5-triazine
2,4,6-tris-(4-hydroxy-3,5-di-t-butylphenoxy)-1,3,5-triazine
n-octadecyl-β-(3,5-di-t-butyl-4-hydroxyphenyl)propionate
n-octadecyl-3,5-di-t-butyl-4-hydroxybenzoate
2-(n-octylthio)ethyl-3,5-di-t-butyl-4-hydroxybenzoate
stearamido N,N-bis-{ethylene 3-(3,5-di-t-butyl-4-hydroxyphenyl)propionate}
1,2-propylene glycol bis-{3-(3,5-di-t-butyl-4-hydroxyphenyl)propionate}
pentaerythritol tetrakis-{3-(3,5-di-t-butyl-4-hydroxyphenyl)propionate}
dioctadecyl-3,5-di-t-butyl-4-hydroxybenzylphosphonate di-n-octadecyl-1-(3,5-di-t-butyl-4hydroxyphenyl)-ethanephosphonate The above phenolic hydrocarbon stabilizers are known and many are commercially available.

The above antioxidants have been listed only for the purpose of illustration and it is important to note that any other antioxidant can be employed with similar improved results. The above exemplified antioxidants and other related antioxidants which are incorporated herein by reference, are disclosed in greater detail in the following patents: Netherlands Patent Specification No. 67/1119, issued Feb. 19, 1968; Netherlands Patent Specification No. 68/03498 issued Sept. 18, 1968; U.S. Pat. Nos. 3,255,191; 3,330,859, 3,644,482, 3,281,505; 3,531,483, 3,285,855; 3,364,250; 3,368,997; 3,357,944 and 3,758,549.

Artificial Light Exposure Test

Deterioration of most polymers caused by ultraviolet light is so slow at ambient temperatures, even in the absence of stabilizers, that testing of the effects of stabilizers generally must be conducted either at higher temperatures or in an accelerated artificial light exposure device in order to yield results in a convenient period of time. The tests conducted in polymers using an artificial light exposure device is described below:

a. Sample Preparation 5 mil Film — Unstabilized polypropylene powder (Hercules Profax 6501) is thoroughly blended with the indicated amounts of additives. The blended material is then milled on a two roll mill for 5 minutes at 182°C. The milled sheet is then compression molded at 220°C into 5 mil thick film under a pressure of 175 psi and water cooled in the press.

b. Testing Method

This test is conducted in a FS/BL unit, basically of the American Cyanamid design, which consists of 40 tubes of alternating fluorescent sunlamps and black lights (20 of each). The 5 mil sample film which are mounted on 3 inches × 2 inches IR card holders with ¼ inch × 1 inch windows and are placed on a rotating drum 2 inches from the bulbs in the FS/BL unit. The time in hours is noted for the development of 0.5 carbonyl absorbance units as determined on an Infrared Spectophotometer. The development of carbonyl functional groups in the polymer is proportional to the amount of degradation caused by the ultraviolet light exposure.

The test results reported below were obtained according to the procedures described above. The amounts of the additives are expressed in weight percent based on the weight of the polymer.

TABLE II

| | Light Stabilization of Polypropylene Time in Hours to 0.5 Carbonyl Absorbance Units | | |
|---|---|---|---|
| Stabilizer | Formul. A | Formul. B | Formul. C |
| 1. Compound of Ex. 1 | 1210 | — | — |
| 2. Compound of Ex. 5 | 1170 | 250 | 695 |
| 3. Compound of Ex. 2 | 1460 | — | — |
| 4. Compound of Ex. 3 | 1280 | 320 | 785 |
| 5. Compound of Ex. 9 | 1345 | — | — |
| 6. Compound of Ex. 11 | 1010 | — | — |
| 7. Compound of Ex. 4 | 1545 | 280 | 850 |
| 8. Compound of Ex. 13 | 1195 | — | — |
| 9. None | | 250 | |

Formulation A contains 0.2% of the indicated stabilizer and 0.5% of UV absorber 2(2'-hydroxy-3',5'-di-tert-butylphenyl)-5-chlorobenzotriazole.

Formulation B contains 0.5% of the indicated stabilizer and 0.2% of di-n-octadecyl 3,5-di-tert-butyl-4-hydroxybenzyl-phosphonate which is an antioxidant.

Formulation C contains 0.25% of the indicated stabilizer, 0.25% of UV absorber 2(2'-hydroxy-3',5'-di-tert-butylphenyl)-5-chlorobenzotriazole and 0.2% of antioxidant di-n-octadecyl 3,5-di-tert-butyl-4-hydroxybenzylphosphonate.

Other hindered phenolic antioxidants may be used in place of di-octadecyl(3,5-di-t-butyl-4-hydroxybenzyl)-phosphonate in the above mentioned compositions for example, di-n-octadecyl α-(3-t-butyl-4-hydroxy-4-methylbenzyl)malonate, 2,4-bis(n-octylthio)-6-(3,4-di-t-butyl-4-hydroxyaniline)-1,3,5-triazine, octadecyl 3-(3',5'-di-t-butyl-4'-hydroxyphenyl)propionate, pentaerythritol-tetrakis{3-(3,5-di-t-butyl-4-hydroxyphenyl)-}propionate, tris-(3,5-di-t-butyl-4-hydroxybenzyl)isocyanurate, 2,6-di-tert-butyl-4-methylphenol, N,N,N-tris-(3,5-di-tert-butyl-4-hydroxybenzyl)isocyanurate, and 2,4,6-tris(3,5-di-tert-butyl-4-hydroxybenzyl)-1,3,5-trimethylbenzyl.

The compositions of Table I are also stabilized with 2(2'-hydroxy-3',5'-di-t-butylphenyl)-5-chlorobenzotriazole is replaced with the following UV absorbers:

a. 2-hydroxy-4-methoxy-5-sulfobenzophenone trihydrate
b. 2-hydroxy-4-n-octoxybenzophenone
c. { 2,2'-thiobis(4-t-octylphenolate)}-n-butylamine nickel II
d. p-octylphenyl salicylate
e. 2,2'-dihydroxy-4,4'-dimethoxybenzophenone
f. 2(2'-hydroxy-5'-methylphenyl)-benzotriazole.

EXAMPLE 14

High impact polystyrene resin containing elastomer (i.e., butadiene-styrene) is stabilized against loss of elongation properties due to exposure to ultraviolet light by incorporation of 0.3% by weight of N-(3,5-dimethyl-4-hydroxyphenyl)-5-norbornene-endo-2,3-dicarboximide.

The unstabilized resin is dissolved in chloroform and the stabilizer then added, after which the mixture is cast on a glass plate and the solvent evaporated to yield a uniform film which, upon drying, is removed and cut up, and then pressed for 7 minutes at a temperature of 163°C and a pressure of 2,000 pounds per square inch into a sheet of uniform thickness (25 mil). The sheets are then cut into strips approximately 4 × 0.5 inches. A portion of these strips is then measured for percent of elongation in the Instron Tensile Testing Apparatus (Instron Engineering Corporation, Quincy, Massachusetts). The remaining portions of the strips are placed in an FS/BL chamber according to Example 7(B) except that the samples are mounted and white cardboard stock and the time to 50% reduction in elongation is measured. The stabilized polystyrene resin retains its elongation property longer than the unstabilized resin.

EXAMPLE 15

Unstabilized linear polyethylene is solvent blended in methylene chloride with 0.5% by weight of the substrate of N-(3-methyl-5-tert-butyl-4-hydroxyphenyl)-norbornane-endo-2,3-dicarboximide and then vacuum dried. The resin is then extrusion compounded on a 1 inch 24/1=L/D extruder, melt temperature 450°F (232°C) and pressed for 7 minutes at a temperature of 163°C and a pressure of 2000 psi into a sheet of uniform thickness of 100 mil. The sheets are then cut into plaques of 2 inch × 2 inch. The plaques are then exposed in a FS/BL exposure device and color measurements made periodically using a Hunter Color Difference Meter Model D25. Polyethylene stabilized with the above compound is found to be much more stable than the unstabilized polyethylene or the polyethylene stabilized only with an antioxidant.

EXAMPLE 16

A quantity of SBR emulsion containing 100 g of rubber (500 ml of 20% SBR obtained from Texas U.S., Synpol 1500) previously stored under nitrogen, is placed in a beaker and stirred vigorously. The pH of the emulsion is adjusted to 10.5 with a 0.5N NaOH solution.

To the emulsion is added 50 ml of 25% NaCl solution. A 6% NaCl solution adjusted with hydrochloric acid to a pH 1.5 is added in a thin stream with vigorous stirring. When pH 6.5 is reached, the rubber begins to coagulate and the addition is slowed down in order to maintain uniform agitation. The addition of the acidic 6% NaCl solution is terminated when a pH 3.5 is reached. The coagulated crumb-rubber slurry at pH 3.5 is stirred for one-half hour.

The coagulated rubber is isolated by filtration through cheese cloth, and rinsed with distilled water. After three subsequent washings with fresh distilled water, the coagulated rubber is dried, first at 25 mm Hg and finally to constant weight under high vacuum (<1 mm) at 40°–45°C.

The dried rubber (25 g) is heated under nitrogen at 125°C in a Brabender mixer and to this is added with mixing 0.5% of N-(3,5-diisopropyl-4-hydroxybenzyl)-norbornane-endo-2,3-dicarboximide. The composition is mixed for 5 minutes after which it is cooled and compression molded at 125°C into 5° × 0.025 inch plaques.

The plaques are exposed to a xenon arc weatherometer and the color measurement (L-b) is made after 45, 125 and 290 hours. The samples stabilized with the above compound are found to be much more light stable than the unstabilized samples.

EXAMPLE 17

To 50 g of polyacetal resin containing 0.1% of an acid scavenger, dicyandiamide, is added 0.2% by weight of N-(3,5-di-tert-butyl-4-hydroxyphenethyl)-5-norbornene-endo-2,3-dicarboximide and milled for 7 minutes at 200°C in a Brabender Plasti-recorder. The milled formulation is subsequently pressed into a 40 mil sheet at 215°C at 350 psi for 90 seconds then cooled quickly in a cold press at 350 psi. The stabilized sheets are then remolded for 2 minutes at contact pressure and for 3 minutes at 300 psi at 215°C to give plaques 1½ inch × 2¼ inch × 125 mil. Thereafter, the testing procedure described above under artificial Light Exposure Test is followed to determine the light stability of the samples. The stabilized samples are found to be much more stable than the unstabilized samples.

EXAMPLE 18

Unstabilized thoroughly dried polyethylene terephthalate chips are dry blended with 1.0% of N-(3,5-di-tert-butyl-4-hydroxyphenyl)-5-norbornene-endo-2,3-dicarboximide. 60/10 denier multifilament is melt spun at a melt temperature of 290°C. The oriented fiber is wound on white cards and exposed in a Xenon Arc Fadeometer. Color measurements are made periodically with a Hunter Color Difference Meter Model D25. The stabilized samples are found to be much more light stable than the unstabilized samples.

EXAMPLE 19 a. A composition comprising acrylonitrilebutadiene-styrene terpolymer and 1% by weight of N-(3,5-di-tert-butyl-4-hydroxyphenyl)-cis-$\Delta^4$-tetra hydrophthalimide resists embrittlement due to exposure to ultraviolet light longer than one which does not contain the stabilizer.

b. A composition comprising polyurethane prepared from toluene diisocyanate and alkylene polyols and 1.0% by weight of N-(3,5-di-tert-butyl-4-hydroxybenzyl)bicyclo[2.2.2]octane-2,3-dicarboximide is more stable to sunlight, fluorescent sunlamps, black lights and fluorescent lights than the unformulated polyurethane.

c. A composition comprising a polycarbonate prepared from bisphenol-A and phosgene and 1% by weight of N-(3,5-di-tert-butyl-4-hydroxyphenyl)-hexahydrophthalimide resists discoloration due to exposure to ultraviolet light longer than one which does not contain the stabilizer.

d. A composition comprising polymethylmethacrylate and 0.25% by weight of N-3,5-di-tert-butyl-4-hydroxybenzyl)-hexadrophthalimide resists discoloration due to exposure to ultraviolet light longer than one which does not contain the stabilizer.

EXAMPLE 20 a. A stabilized polyamide (nylon 6, 6) is prepared by incorporating therein 0.1% of N-(3,5-di-tert-butyl-4-hydroxyphenyl)-4,5-epoxyhexahydrophthalimide. The light stability of the stabilized composition is superior to that of an unstabilized polyamide.

b. A stabilized polyphenylene oxide polymer (prepared by polymerizing 2,6-dimethylphenol is prepared by incorporating therein 0.5% by weight of the manganese complex of N-(3,5-di-tert-butyl-4-hydroxy-benzyl)-5,6-epoxy-5-norbornane-endo-2,3-dicarboximide. The stabilized compositions resist embrittlement due to exposure to ultraviolet light longer than one which does not contain the stabilizer.

c. A stabilized crystalline polystyrene is prepared by incorporating therein 0.1% by weight of N-(3,5-dimethyl-4-hydroxybenzyl)-hexahydrophthalimide. The stabilized composition resists embrittlement due to exposure to ultraviolet light longer than one which does not contain the stabilizer.

What is claimed is:

1. A composition of matter comprising
   a. an organic material normally subject to degradation,
   b. from 0.01 to 5% of a stabilizer of the formula

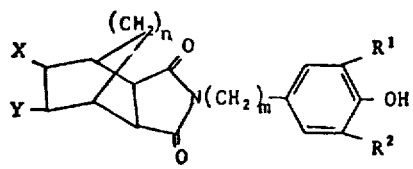   I wherein $R^1$ and $R^2$ are the same or different (lower) alkyl groups of 1 to 4 carbon atoms,
   X and Y are hydrogen or, when taken together, they form a bond or an ether linkage,
   $m$ has a value of 0 to 3, and
   $n$ has a value of 0 to 2.
   c. from 0 to 5% of a UV absorber, and
   d. from 0 to 5% of a co-stabilizer.

2. A composition of claim 1, wherein the organic material is polyolefin.

3. A composition of claim 2, wherein in the stabilizer $R^1$ and $R^2$ are tert-butyl.

4. A composition of claim 3 wherein the organic material is polypropylene.

* * * * *